(12) United States Patent
Watabe et al.

(10) Patent No.: US 10,330,646 B2
(45) Date of Patent: Jun. 25, 2019

(54) STRUCTURE EVALUATION SYSTEM, STRUCTURE EVALUATION APPARATUS, AND STRUCTURE EVALUATION METHOD

(71) Applicants: Kabushiki Kaisha Toshiba, Tokyo (JP); Kyoto University, Kyoto (JP)

(72) Inventors: Kazuo Watabe, Kanagawa (JP); Hidefumi Takamine, Tokyo (JP); Tomoki Shiotani, Kyoto (JP)

(73) Assignees: Kabushiki Kaisha Toshiba, Tokyo (JP); Kyoto University, Kyoto (JP)

( * ) Notice: Subject to any disclaimer, the term of this patent is extended or adjusted under 35 U.S.C. 154(b) by 108 days.

(21) Appl. No.: 15/454,101

(22) Filed: Mar. 9, 2017

(65) Prior Publication Data

US 2017/0336364 A1    Nov. 23, 2017

Related U.S. Application Data

(63) Continuation of application No. PCT/JP2017/008818, filed on Mar. 6, 2017.

(30) Foreign Application Priority Data

May 17, 2016    (JP) .................................. 2016-098951

(51) Int. Cl.
  *G01M 5/00*    (2006.01)
  *G01N 29/04*    (2006.01)
  (Continued)

(52) U.S. Cl.
  CPC .......... *G01N 29/14* (2013.01); *G01M 5/0008* (2013.01); *G01M 5/0033* (2013.01);
  (Continued)

(58) Field of Classification Search
  CPC ............ G01M 5/0008; G01M 5/0033; G01M 5/0066; G01N 29/14; G01N 29/4445;
  (Continued)

(56) References Cited

U.S. PATENT DOCUMENTS

| 4,531,411 A | 7/1985 | Collins et al. |
| 5,293,555 A | 3/1994 | Anthony et al. |

(Continued)

FOREIGN PATENT DOCUMENTS

| CN | 102269736 A | 12/2011 |
| JP | 8-313309 A | 11/1996 |

(Continued)

OTHER PUBLICATIONS

Office Action dated Sep. 13, 2018 in U.S. Appl. No. 15/456,075.

*Primary Examiner* — Jacques M Saint Surin
(74) *Attorney, Agent, or Firm* — Oblon, McClelland, Maier & Neustadt, L.L.P.

(57) ABSTRACT

According to an embodiment, a structure evaluation system includes a plurality of AE sensors, a signal processor, a position locator, a velocity calculator, and an evaluator. The AE sensors detect an elastic wave generated from a structure. The signal processor extracts an AE signal including information on the elastic wave by performing signal processing on the elastic wave detected by the AE sensor. The position locator derives a wave source distribution indicating a distribution of sources of the elastic waves generated in the structure on the basis of the AE signals. The velocity calculator derives a propagation velocity of the elastic wave generated in the structure on the basis of the AE signal. The evaluator evaluates the soundness of the structure on the basis of the wave source distributions and the propagation velocity of the elastic waves.

10 Claims, 10 Drawing Sheets (51) Int. Cl.
*G01N 29/07* (2006.01)
*G01N 29/14* (2006.01)
*G01N 29/24* (2006.01)
*G01N 29/44* (2006.01)

(52) U.S. Cl.
CPC ........ *G01M 5/0066* (2013.01); *G01N 29/043* (2013.01); *G01N 29/07* (2013.01); *G01N 29/2437* (2013.01); *G01N 29/4436* (2013.01); *G01N 29/4445* (2013.01); *G01N 29/4463* (2013.01); *G01N 2291/0232* (2013.01); *G01N 2291/0258* (2013.01); *G01N 2291/0289* (2013.01)

(58) Field of Classification Search
CPC ............... G01N 29/07; G01N 29/2437; G01N 29/4463; G01N 29/043; G01N 29/4436; G01N 2291/0258; G01N 2291/0289; G01N 2291/0232
USPC ........................................................ 73/587
See application file for complete search history.

(56) References Cited

U.S. PATENT DOCUMENTS

| | | | | |
|---|---|---|---|---|
| 6,957,583 | B2* | 10/2005 | Tooma | B06B 1/06 600/448 |
| 7,719,689 | B2* | 5/2010 | Lee | G01L 1/246 356/479 |
| 2013/0118261 | A1 | 5/2013 | Stothers et al. | |
| 2015/0338380 | A1 | 11/2015 | Ziehl et al. | |
| 2017/0336365 | A1* | 11/2017 | Watabe | G01M 5/0008 |
| 2017/0363586 | A1 | 12/2017 | Takamine et al. | |
| 2017/0363587 | A1 | 12/2017 | Takamine et al. | |
| 2018/0074019 | A1* | 3/2018 | Iida | G01N 29/07 |

FOREIGN PATENT DOCUMENTS

| | | | |
|---|---|---|---|
| JP | 9-218182 | A | 8/1997 |
| JP | 2004-125721 | A | 4/2004 |
| JP | 2004-170397 | A | 6/2004 |
| JP | 2014-095555 | A | 5/2014 |
| JP | 2014095555 | * | 5/2014 |
| JP | 6171214 | * | 8/2017 |

* cited by examiner

STRUCTURE EVALUATION SYSTEM, STRUCTURE EVALUATION APPARATUS, AND STRUCTURE EVALUATION METHOD

TECHNICAL FIELD

The present invention relates to a structure evaluation system, a structure evaluation apparatus, and a structure evaluation method.

BACKGROUND ART

In recent years, problems related to aging of structures such as bridges constructed during the period of high economic growth have become noticeable. Because loss is immeasurable when an accident occurs in a structure, technologies for monitoring a state of a structure have been proposed. For example, a technology for detecting damage to a structure by an acoustic emission (AE) method in which an elastic wave generated due to occurrence of an internal crack or development of an internal crack is detected by a high-sensitivity sensor has been proposed. AE is an elastic wave generated due to development of fatigue crack of a material. In the AE method, an elastic wave is detected as an AE signal (voltage signal) by an AE sensor using a piezoelectric element. The AE signal is detected as an indication before breakage of the material occurs. Therefore, the frequency of occurrence of AE signals and the signal intensity are used as an index indicating the soundness of the material. For this reason, studies are being carried out on technologies for detecting signs of deterioration of structures by the AE method.

When a load doe to traffic or the like is applied on a concrete floor slab of a bridge, AE occurs due to crack propagation, friction, or the like in the floor slab. By installing an AE sensor on a surface of the floor slab, the AE generated from the floor slab can be detected. Moreover, by installing a plurality of AE sensors, a position of an AE source can be located from a difference in arrival time of AE signals between the AE sensors. A degree of damage to a target floor slab is estimated from the result of locating the position of the AE source. However, when the correspondence between the location result and the degree of damage is not sufficient, stable soundness evaluation cannot be performed in some cases. Such a problem is not limited to concrete floor slabs of a bridge but is a problem common to all structures in which elastic waves are generated as cracks occur or develop.

CITATION LIST

Patent Literature

[Patent Literature 1]
Japanese Unexamined Patent Application, First Publication No. 2004-125721

SUMMARY OF INVENTION

Technical Problem

An objective of the present invention is to provide a structure evaluation system, a structure evaluation apparatus, and a structure evaluation method capable of evaluating soundness of a structure in which elastic waves are generated.

Solution to Problem

According to an embodiment, a structure evaluation system includes a plurality of AE sensors, a signal processor, a position locator, a velocity calculator, and an evaluates. The AE sensors detect an elastic wave generated from a structure. The signal processor extracts an AE signal including information on the elastic wave by performing signal processing on the elastic wave detected by the AE sensor. The position locator derives a wave source distribution indicating a distribution of sources of the elastic waves generated in the structure on the basis of the AE signals. The velocity calculator derives a propagation velocity of the elastic wave generated in the structure on the basis of the AE signal. The evaluator evaluates the soundness of the structure on the basis of the wave source distributions and the propagation velocity of the elastic waves.

DESCRIPTION OF EMBODIMENTS

Hereinafter, a structure evaluation system, a structure evaluation apparatus, and a structure evaluation method according to an embodiment will be described with reference to the accompanying drawings.

Figure 1:
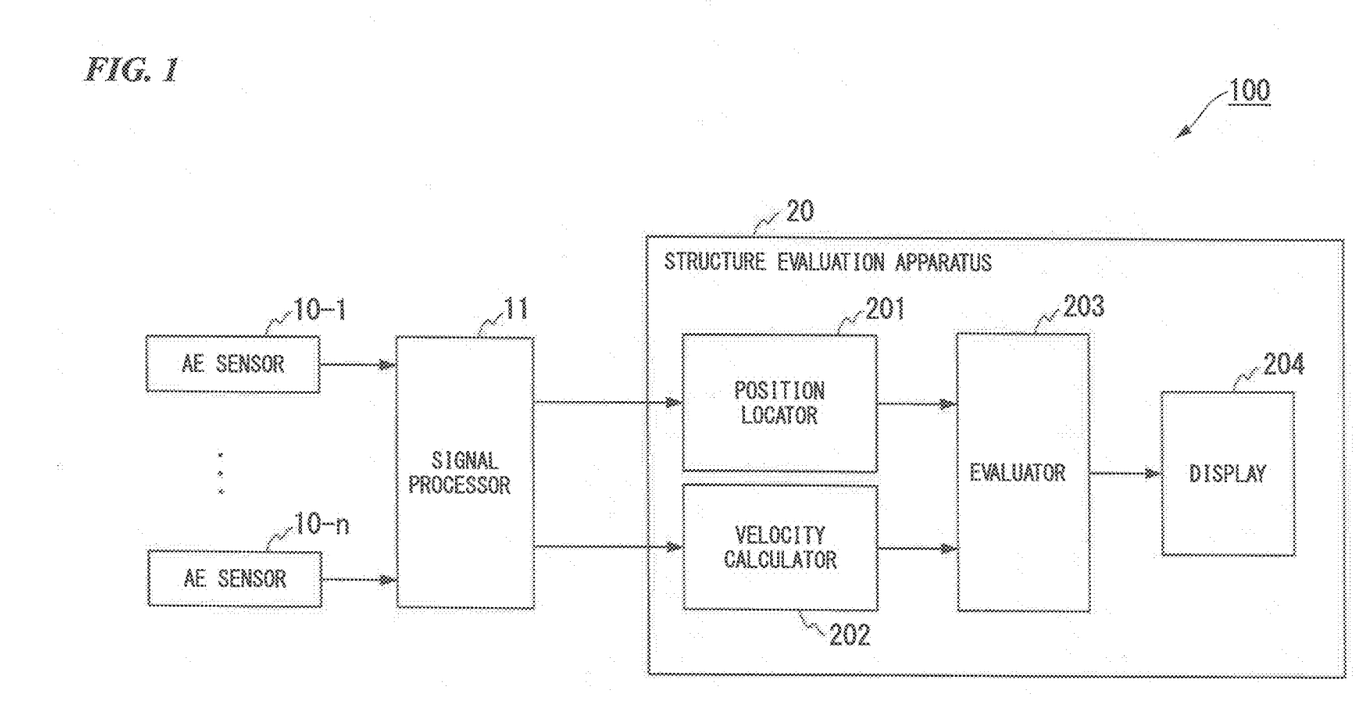
FIG. 1 is a view illustrating a system constitution of a structure evaluation system 100 according to an embodiment.

FIG. 1 is a view illustrating a system constitution of a structure evaluation system 100 according to an embodiment. The structure evaluation system 100 is used for evaluating the soundness of a structure. Although a bridge is described as an example of a structure in the embodiment, a structure is not necessarily limited to a bridge. For example, a structure may be any structure as long as an elastic wave is generated in the structure due to occurrence or development of cracks or an external impact (e.g., rain, artificial rain, etc.). Also, a bridge is not limited to a structure constructed over a river or a valley, and includes various structures provided above the ground (e.g., an elevated bridge over a highway).

The structure evaluation system 100 includes a plurality of acoustic emission (AE) sensors 10-1 to 10-n (n is an integer equal to or greater than 2), a signal processor 11, and a structure evaluation apparatus 20. The signal processor 11 and the structure evaluation apparatus 20 are connected to be able to communicate via a wire or wireless. Further, in the description below, the AE sensors 10-1 to 10-n are referred to as an AE sensor 10 when not distinguished.

The AE sensor 10 is installed in a structure. For example, the AE sensor 10 is installed on a concrete floor slab of a bridge. The AE sensor 10 has a piezoelectric element, detects an elastic wave (an AE wave) generated from the structure, and converts the detected elastic wave into a voltage signal (an AE source signal). The AE sensor 10 performs processing such as amplification and frequency limiting on the AE source signal and outputs the processing result to the signal processor 11.

The signal processor 11 receives the AE source signal processed by the AE sensor 10 as an input. The signal processor 11 performs signal processing, such as noise removal and parameter extraction, deemed necessary on the input AE source signal to extract an AE feature amount including information on the elastic wave. The information on the elastic wave is, for example, information such as an amplitude, an energy, a rise time, a duration, a frequency, and a zero-crossing count number of the AE source signal. The signal processor 11 outputs information based on the extracted AE feature amount to the structure evaluation apparatus 20 as an AE signal. The AE signal output from the signal processor 11 includes information such as a sensor ID, an AE detection time, an AE source signal amplitude, an energy, a rise time, and a frequency.

Here, the amplitude of the AE source signal is, for example, a value of the maximum amplitude among elastic waves. The energy is, for example, a value obtained by time integration of squared amplitude at each time point. The definition of energy is not limited to the above example, and may be, for example, one approximated by using an envelope curve of a waveform. The rise time is, for example, a time T1 until an elastic wave rises above a preset predetermined value from zero. The duration is, for example, an amount of time from the start of the rise of an elastic wave until the amplitude becomes smaller than a preset value. The frequency is a frequency of an elastic wave. The zero-crossing count number is, for example, the number of times that a wave crosses a reference line passing a zero value.

The structure evaluation apparatus 20 includes a central processing unit (CPU), a memory, an auxiliary storage device or the like connected via a bus, and executes an evaluation program. By executing the evaluation program, the structure evaluation apparatus 20 functions as an apparatus including a position locator 201, a velocity calculator 202, an evaluator 203, and a display 204. Further, all or some of the functions of the structure evaluation apparatus 20 may be realized by using hardware such as an application specific integrated circuit (ASIC), a programmable logic device (PLD), a field programmable gate array (FPGA), or the like. Also, the evaluation program may be recorded in a computer-readable recording medium. The computer-readable recording medium is, for example, a portable medium such as a flexible disk, a magneto-optical disk, a read-only memory (ROM), a compact disc (CD)-ROM or the like, or a storage device such as a hard disk embedded in a computer system. Also, the evaluation program may be transmitted and received via an electric communication line.

The position locator 201 receives an AE signal output from the signal processor 11 as an input. Also, the position locator 201 pre-stores information on an installation position of the AE sensor 10 in the structure (hereinafter referred to as "sensor position information") by matching the information to a sensor ID. The information on the installation position is, for example, latitude and longitude, or a distance in the horizontal direction and the vertical direction from a specific position on the structure, and the like. The position locator 201 locates a position of an AE source on the basis of the information such as the sensor ID and the AE detection time included in the input AE signal and the pre-stored sensor position information. The position locator 201 derives (calculates) an AE source density distribution (wave source distribution) by using the position location results for a certain period. The AE source density distribution represents the distribution showing the wave sources of the elastic waves generated in the structure. The position locator 201 outputs the derived AE source density distribution to the evaluator 203.

The velocity calculator 202 receives the AE signal output from the signal processor 11 as an input. Also, the velocity calculator 202 pre-stores the sensor position information by matching the sensor position information to a sensor ID. The velocity calculator 202 derives an elastic wave propagation velocity distribution of the structure on the basis of the information such as the sensor IDs and the AE detection times included in the input AE signals and the pre-stored sensor position information. The elastic wave propagation velocity distribution represents a distribution showing the propagation velocity of the elastic waves generated in the structure. For example, the velocity calculator 202 derives the elastic wave propagation velocity distribution of the structure using an AE tomography analysis method. The velocity calculator 202 outputs the derived elastic wave propagation velocity distribution to the evaluator 203. The AE tomography analysis method is a method in which elastic waves generated from a structure are detected by a plurality of AE sensors, a position of an AE source is located, and propagation velocities of an analysis model of the structure is corrected so that an error between a theoretical traveling time and a measured traveling time from the source to each sensor converges to within a tolerance range, to obtain the elastic wave propagation velocity distribution in the structure. Because a velocity of AE traveling inside decreases as a structure deteriorates, the degree of deterioration inside the structure can be evaluated from the AE velocity distribution by using the AE tomography analysis method.

The evaluator 203 receives the AE source density distribution output from the position locator 201 and the elastic wave propagation velocity distribution output from the velocity calculator 202 as inputs. The evaluator 203 evaluates the soundness of the structure on the basis of the input AE source density distribution and elastic wave propagation velocity distribution. The evaluator 203 makes the display 204 display the evaluation result.

The display 204 is an image display device such as a liquid crystal display or an organic electro-luminescence (EL) display. The display 204 displays an evaluation result in accordance with the control of the evaluator 203. The display 204 may be an interface for connecting the image display device to the structure evaluation apparatus 20. In this case, the display 204 generates an image signal for displaying the evaluation result and outputs the image signal to the image display device connected thereto.

Figure 2A:
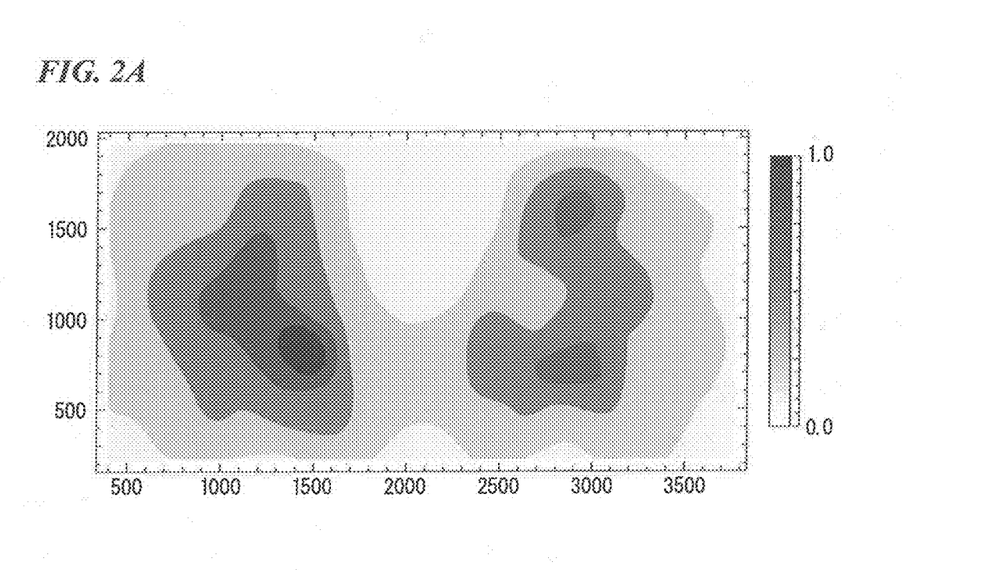
FIG. 2A is a view illustrating a specific example of an AE source density distribution.
Figure 2B:
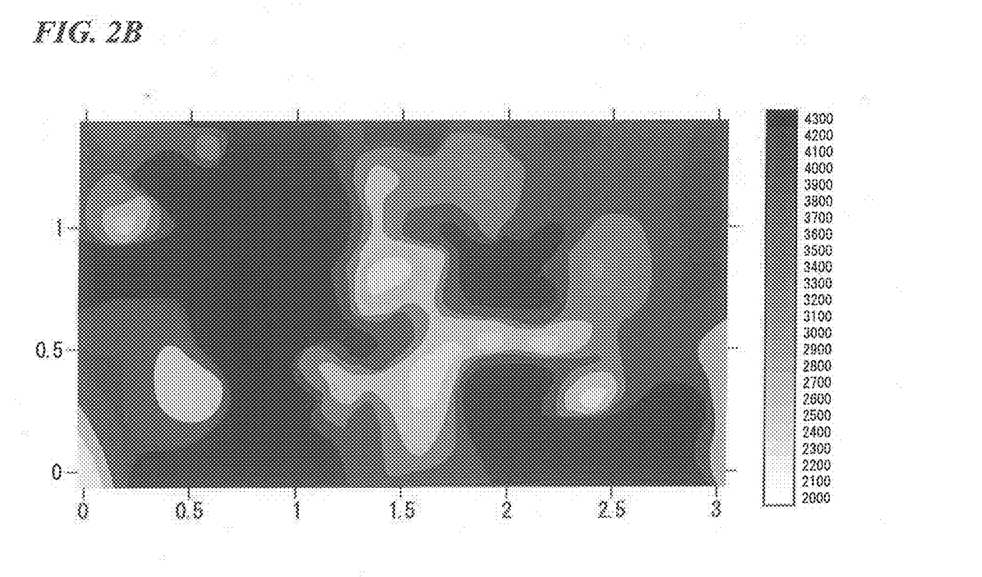
FIG. 2B is a view illustrating an elastic wave propagation velocity distribution.

FIG. 2A shows the AE source density distribution, and FIG. 2B shows the elastic wave propagation velocity distribution. The AE source density distribution and the elastic wave propagation velocity distribution are distributions obtained on the basis of the same region of the same structure. FIGS. 2A and 2B illustrates a result of using fifteen AE sensors 10 on a floor slab of a structure of a certain road. In FIG. 2A, the horizontal axis and the vertical axis represent the length (mm) in the horizontal direction from a specific position on the structure to be evaluated and the length (mm) in the vertical direction from the specific position on the structure to be evaluated. Further, in FIG. 2B, the horizontal axis and the vertical axis represent the horizontal length (m) and the vertical length (m) from a specific position on the structure to be evaluated.

In FIG. 2A, a region is shown more darkly as the number of wave sources becomes larger (as the wave sources become more densely arranged), and a region is shown more lightly as the number of wave sources becomes smaller (as the wave sources becomes more sparsely arranged). For example, a region 30 in FIG. 2A represents a region in which the number of wave sources is larger than in other regions. Further, in FIG. 2B, a region is shown more darkly as the propagation velocity becomes higher, and a region is shown more lightly as the propagation velocity becomes lower. The AE source density distribution and the elastic wave propagation velocity distribution shown in FIGS. 2A and 2B are input to the evaluator 203.

Hereinafter, with reference to FIGS. 3A, 3B and 4, specific processing of the evaluator 203 will be described.

On the basis of a reference value related to the density of the wave sources (hereinafter referred to as "density reference value"), the evaluator 203 segments the input AE source density distribution into two regions, including a region in which the wave sources are sparsely arranged and a region in which the wave sources are densely arranged. Specifically, the evaluator 203 segments the AE source density distribution by binarizing the AE source density distribution on the basis of the density reference value. In the embodiment, the density reference value is set as 0.5. The evaluator 203 segments the AE source density distribution by binarizing a region having a density higher than the density reference value as a region in which the wave sources are densely arranged and a region having a density lower than the density reference value as region in which the wave sources are sparsely arranged. The density reference value is not necessarily limited to the above value and may be appropriately changed.

Further, on the basis of a reference value related to the propagation velocity of the wave source (hereinafter referred to as "propagation velocity reference value"), the evaluator 203 segments the input elastic wave propagation velocity distribution into two regions, including a region in which the propagation velocity is high and a region in which the propagation velocity is low. Specifically, the evaluator 203 segments the elastic wave propagation velocity distribution by binarizing the elastic wave propagation velocity distribution on the basis of the propagation velocity reference value. In the embodiment, the propagation velocity reference value is set as 3800 m/s. The evaluator 203 segments the elastic wave propagation velocity distribution by binarizing a region having a propagation velocity higher than the propagation velocity reference value as a region in which the propagation velocity is high and a region having a propagation velocity lower than the propagation velocity reference value as a region in which the propagation velocity is low. The propagation velocity reference value is not necessarily limited to the above value and may be appropriately changed.

Figure 3A:
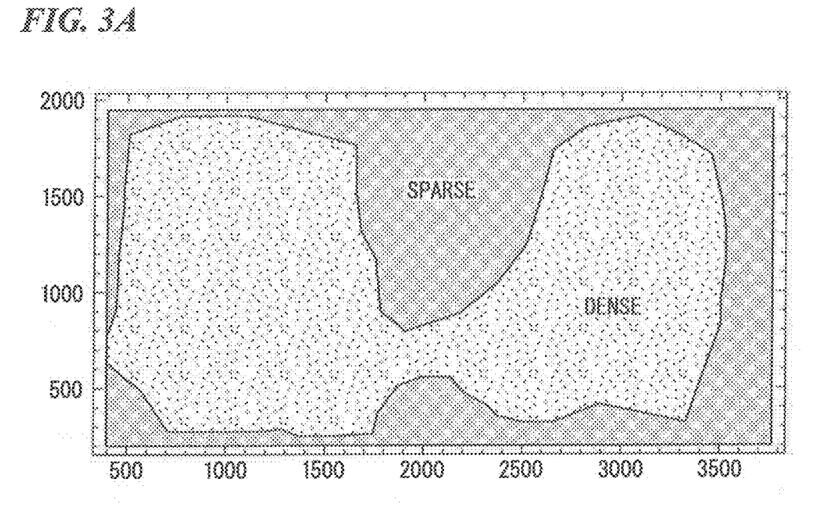
FIG. 3A is a view illustrating a region segmentation result of an AE source density distribution.
Figure 3B:
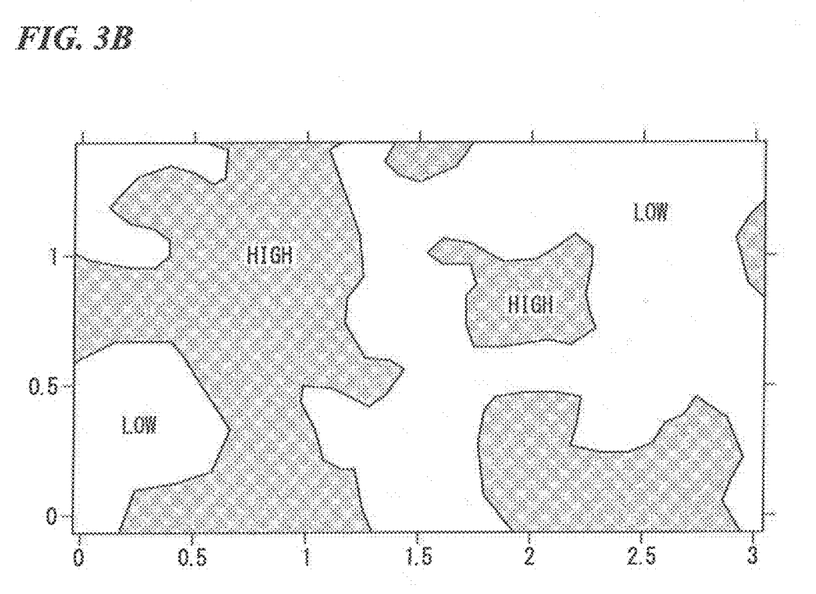
FIG. 3B is a view illustrating a region segmentation result of an elastic wave propagation velocity distribution.

FIG. 3A shows a region segmentation result of the AE source density distribution, and FIG. 3B shows a region segmentation result of the elastic wave propagation velocity distribution. Hereinafter, the view shown in FIG. 3A is described as a binarized AE source density distribution, and the view shown in FIG. 3B is described as a binarized elastic wave propagation velocity distribution.

Then, the e valuator 203 evaluates the soundness of the structure using the binarized AE source density distribution and the binarized elastic wave propagation velocity distribution. Specifically, the evaluator 203 superimposes the binarized AE source density distribution and the binarized elastic wave propagation velocity distribution to evaluate the soundness of the structure as four phases according to the result of segmentation of the superimposed region. Here, a specific example of the four phases for evaluation may include Sound, Intermediate deterioration I, Intermediate deterioration II and Limit deterioration. Sound, Intermediate deterioration I, Intermediate deterioration II, and Limit deterioration represent a progress of deterioration of a structure in that order. In other words, Sound indicates that the deterioration of the structure has not progressed most, and a phase approaching Limit deterioration indicates that the deterioration of the structure has progressed. Based on the following evaluation conditions, the evaluator 203 evaluates to which of Sound, intermediate deterioration I, Intermediate deterioration II, and Limit deterioration each region (each of the superimposed regions) of the structure corresponds.

(Evaluation Conditions)

Sound: "sparse" region in the binarized AE source density distribution and "high" region in the binarized elastic wave propagation velocity distribution Intermediate deterioration I: "dense" region in the binarized AE source density distribution and "high" region in the binarized elastic wave propagation velocity distribution Intermediate deterioration II: "dense" region in the binarized AE source density distribution and "low" region in the binarized elastic wave propagation velocity distribution Limit deterioration: "sparse" region in the binarized AE source density distribution and "low" region in the binarized elastic wave propagation velocity distribution As described above, when the superimposed region is a region in which the wave sources are sparsely arranged and a region in which the propagation velocity is high, the evaluator 203 evaluates the region as a region in a Sound phase. When the superimposed region is a region in which the wave sources are densely arranged and a region in which the propagation velocity is high, the evaluator 203 evaluates the region as a region in an Intermediate deterioration I phase. Further, when the superimposed region is a region in which the wave sources are densely arranged and the propagation velocity is low, the evaluator 203 evaluates that region as a region in an Intermediate deterioration II phase. Further, when the superimposed region is a region in which the wave sources are sparsely arranged and the propagation velocity is low, the evaluator 203 evaluates the region as a region in a Limit deterioration phase.

As described above, by evaluating to which of Sound, Intermediate deterioration I, Intermediate deterioration II, and Limit deterioration each of the superimposed regions corresponds, the evaluator 203 derives an evaluation result distribution in which an evaluation result of each of the regions is shown. For example, in the evaluation result distribution, the evaluator 203 indicates a region in a Sound phase as "1", a region in an Intermediate deterioration I phase as "2", a region in an Intermediate deterioration II phase as "3", and a region in a Limit deterioration phase as "4." The evaluator 203 makes the display 204 display the derived evaluation result distribution.

Figure 4:
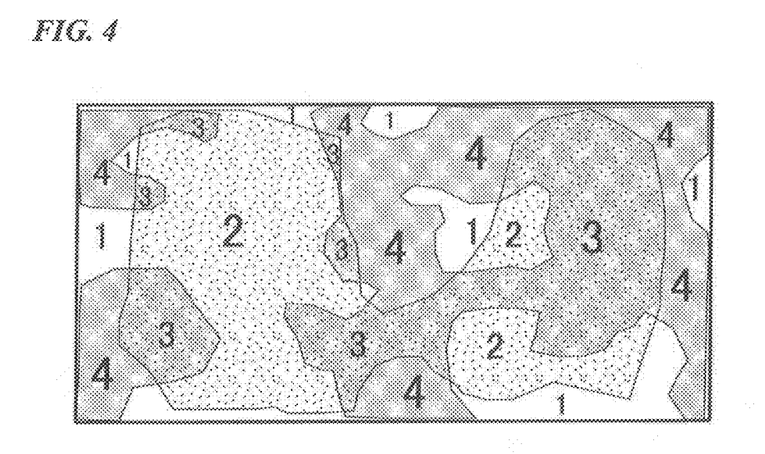
FIG. 4 is a view illustrating an example of an evaluation result distribution.

FIG. 4 is a view illustrating an example of the evaluation result distribution. An operator or a manager can easily find out which region of a structure is deteriorating with the evaluation result distribution displayed as illustrated in FIG. 4.

Figure 5:
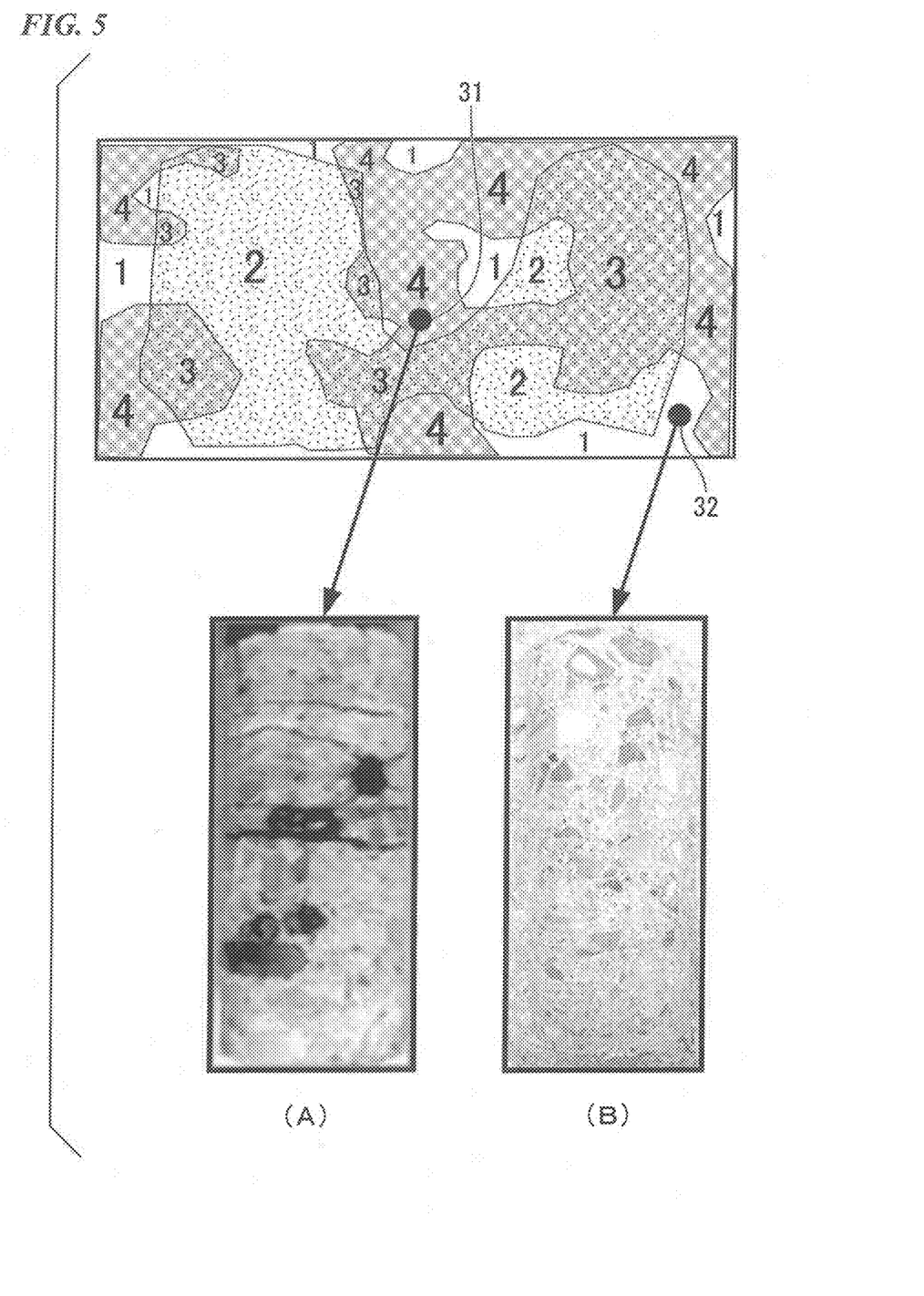
FIG. 5 is a view illustrating a verification result of the validity of the evaluation result.

FIG. 5 is a view illustrating a verification result of the validity of the evaluation result. FIG. 5 shows results of collecting and checking the inside of a floor slab of the structure shown in FIG. 4. FIG. 5 shows a core sample collected from a portion of a circle 31 in the region "4" indicating a Limit deterioration phase in FIG. 4. As illustrated in FIG. 5, it can be seen that deterioration inside the core sample has progressed to an extent that the core may be separated due to horizontal cracks. On the other hand. FIG. 5 shows a core sample collected from a portion of a circle 32 in the region "1" indicating a Sound phase in FIG. 4. As illustrated in FIG. 5, cracks are not seen with visual observation inside the core sample. Thus, the effectiveness of the evaluation method with the structure evaluation apparatus 20 is confirmed.

Figure 6:
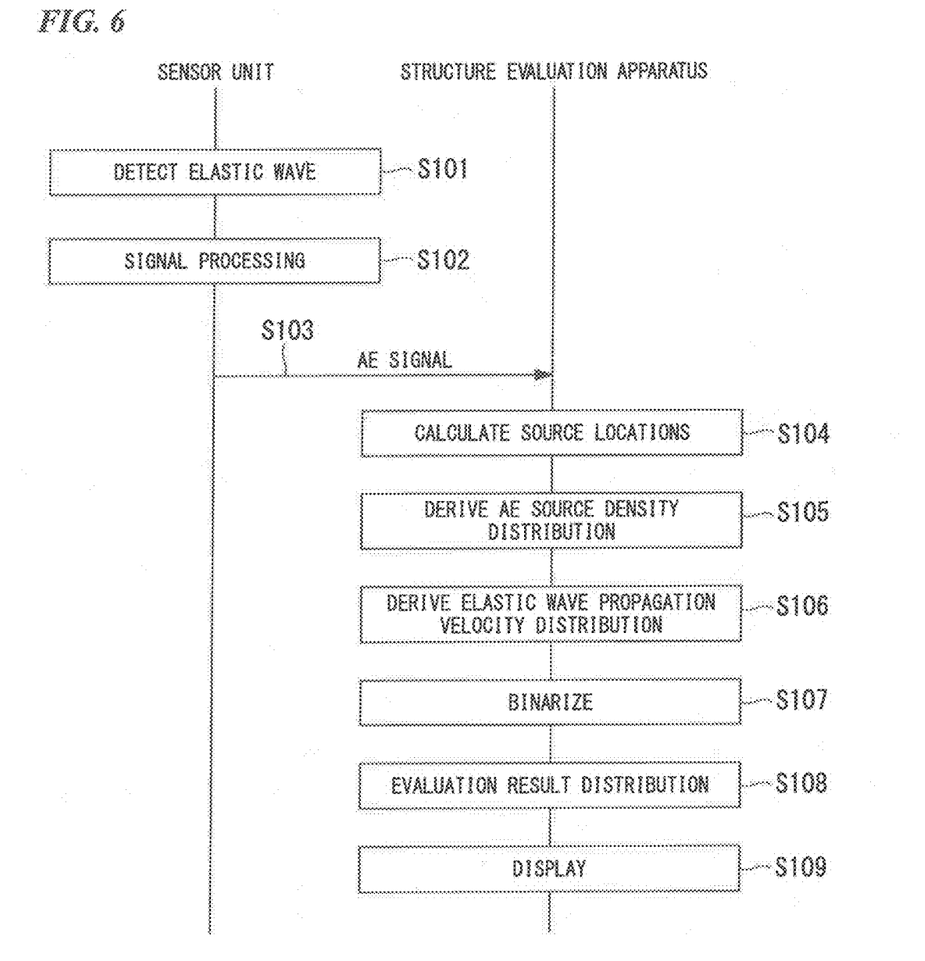
FIG. 6 is a sequence diagram illustrating a process flow of a structure evaluation system 100.

FIG. 6 is a sequence diagram illustrating the process flow of the structure evaluation system 100. In FIG. 6, each of the AE sensors 10 and the signal processor 11 is a sensor unit.

Each of the AE sensors 10 detects an elastic wave (an AE wave) generated by a structure (Step S101). The AE sensor 10 converts the detected elastic wave into a voltage signal (an AE source signal), performs processing such as amplification and frequency limiting on the AE source signal, and outputs the result to the signal processor 11. The signal processor 11 performs signal processing, such as noise removal and parameter extraction, deemed necessary on the input AE source signal (Step S102). The signal processor 11 outputs information based on an AE feature amount extracted by performing signal processing to the structure evaluation apparatus 20 as an AE signal (Step S103). The process from Step S101 to Step S103 is executed for a predetermined period.

The position locator 201 locates a position of the AE source on the basis of the AE signal output from the signal processor 11 and the pre-stored sensor position information (Step S104). The position locator 201 executes the process of Step S104 for a predetermined period. Then, the position locator 201 derives the AE source density distribution using the position location results for the predetermined period (Step S105). The position locator 201 outputs the derived AE source density distribution to the evaluator 203.

Based on the AE signals output from the signal processor 11, the velocity calculator 202 derives the elastic wave propagation velocity distribution of the structure (Step S106). For example, the velocity calculator 202 may derive the elastic wave propagation velocity distribution using the AE signals for a predetermined period, or may derive the elastic wave propagation velocity distribution using AE signals for a period shorter than the predetermined period. The velocity calculator 202 outputs the derived elastic wave propagation velocity distribution to the evaluator 203. Step S105 and Step S106 may be performed in any order.

The evaluator 203 derives the binarized AE source density distribution and the binarized elastic wave propagation velocity distribution by binarizing each of the AE source density distribution output from the position locator 201 and the elastic wave propagation velocity distribution output from the velocity calculator 202 (Step S107). Using the derived binarized AE source density distribution and binarized elastic wave propagation velocity distribution, the evaluator 203 derives the evaluation result distribution by evaluating each region of the structure on the basis of the evaluation conditions (Step S108). The evaluator 203 makes the display 204 display the derived evaluation result distribution. The display 204 displays the evaluation result distribution according to control of the evaluator 203 (Step S109).

Figure 7:
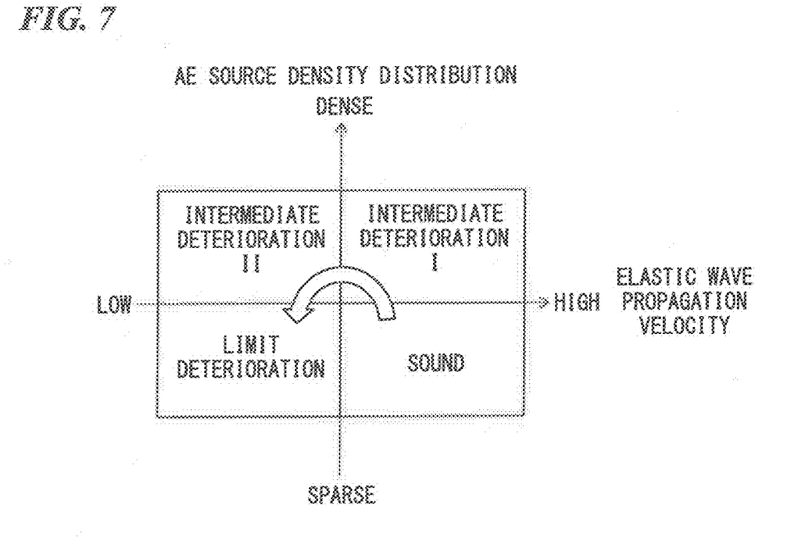
FIG. 7 is a view illustrating a basic concept of soundness evaluation using a structure evaluation apparatus 20 according to the embodiment.

FIG. 7 is a view illustrating a basic concept of soundness evaluation using the structure evaluation apparatus 20 according to the present embodiment. As illustrated in FIG. 7, in the structure evaluation apparatus 20 according to the present embodiment, the high and low level of the elastic wave propagation velocity and the degree of the AE source density each are on two-dimensional evaluation axes which are divided into 4 quadrants. Then, the structure evaluation apparatus 20 distinguishes the four quadrants as Sound, Intermediate deterioration I, Intermediate deterioration II, and Limit deterioration on the basis of the evaluation conditions. Here, conventional evaluation methods are compared with the evaluation method according to the embodiment.

Figure 8A:
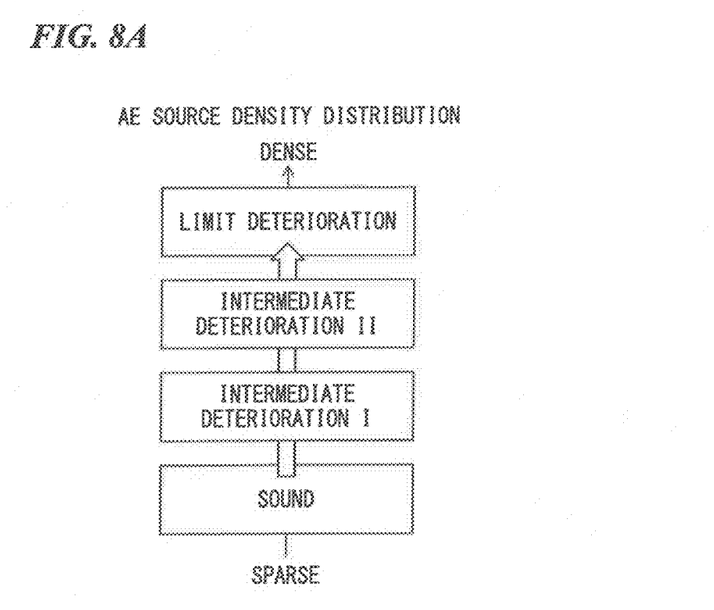
FIG. 8A is a view illustrating conventional examples of evaluating soundness of a structure.
Figure 8B:
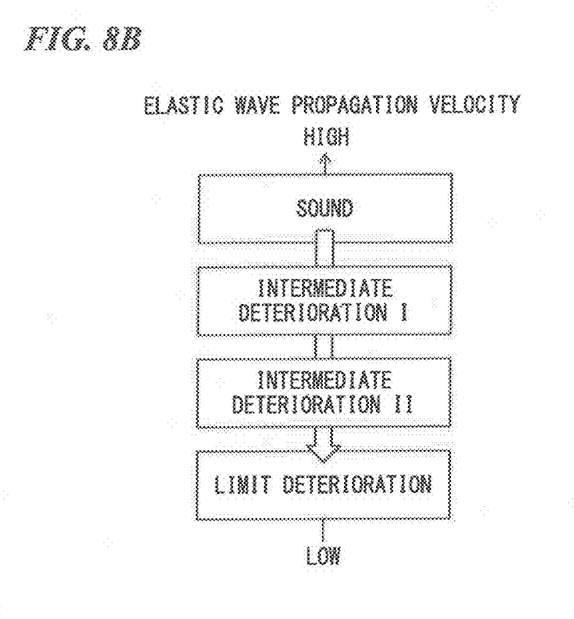
FIG. 8B is a view illustrating conventional examples of evaluating soundness of a structure.

FIG. 8A shows evaluation based only on AE source location, and FIG. 8B shows evaluation based only on the propagation velocity. As illustrated in FIG. 8A, in the evaluation based only on AE source location, the probability that the structure has deteriorated becomes higher as AE sources become more densely arranged. Further, as illustrated in FIG. 8B, in the evaluation based only on the propagation velocity, the probability that the structure has deteriorated becomes higher as the propagation velocity becomes lower.

Figure 9:
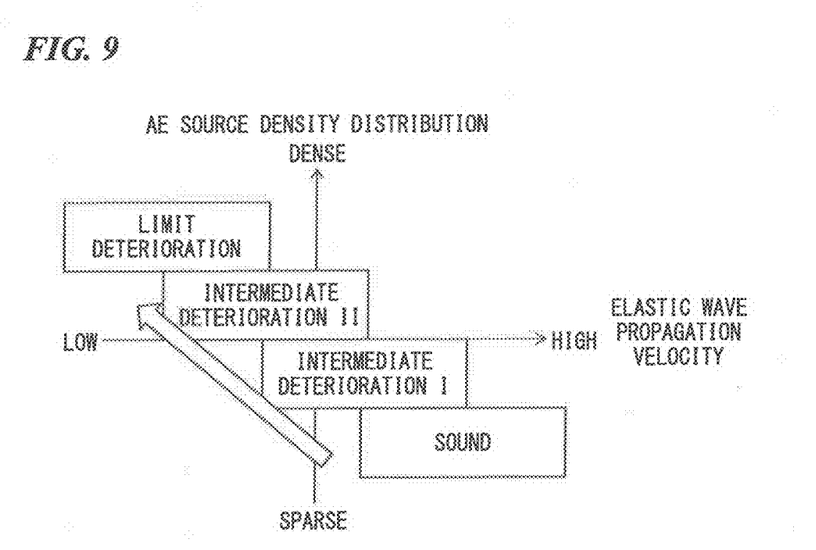
FIG. 9 is a view illustrating an example of an evaluation result when it is assumed that two conventional evaluation methods shown in FIGS. 8A and 8B are combined.

FIG. 9 is a view illustrating an example of an evaluation result when it is assumed foal the two conventional evaluation methods shown in FIGS. 8A and 8B are combined. As illustrated in FIG. 9, when the two conventional evaluation methods are simply combined, a linear change is expected in which a region in which the elastic wave propagation velocity is higher than a certain reference and the AE source density distribution is sparse (a region in which the wave sources are sparsely arranged) is in a Sound phase, and a region in which the elastic wave propagation velocity is lower than the certain reference and the AE source density distribution is dense (the wave sources are densely arranged) has deteriorated and reached a Limit deterioration phase. This is not always a correct evaluation index because it has been experimentally confirmed that a structure in the Limit deterioration state may still have a sparse AE source density distribution and a structure which has deteriorated to some extent may still have an elastic wave propagation velocity that is substantially the same as that in the Sound state. On the other hand, the basic concept of soundness evaluation by the structure evaluation apparatus 20 according to the embodiment illustrated in FIG. 7 may be considered as a correct evaluation index, as can also be seen from the verification result of the validity of the evaluation result illustrated in FIG. 5.

According to the structure evaluation system 100 configured as described above, the soundness of a structure that generates an elastic wave can be evaluated. Hereinafter, an effect thereof will be described in detail.

The structure evaluation apparatus 20 evaluates the soundness of the structure on the basis of the evaluation conditions using the AE source density distribution obtained from the elastic wave detected by each of the plurality of AE sensors 10 and the elastic wave propagation velocity distribution. As described above, the structure evaluation apparatus 20 according to the embodiment can evaluate a deterioration level for each region of the structure by combining the AE source density distribution and the elastic wave propagation velocity distribution. Therefore, the soundness of the structure generating elastic waves can be evaluated. Also, the structure evaluation apparatus 20 can evaluate with higher accuracy by using a plurality of pieces of information instead of one piece of information obtained from elastic waves.

Hereinafter, a modified example of the structure evaluation apparatus 20 will be described.

Part or all of functional units of the structure evaluation apparatus 20 may be provided in separate housings. For example, the structure evaluation apparatus 20 may include only the evaluator 203, and the position locator 201, the velocity calculator 202, and the display 204 may be provided in separate housings. In this case, the evaluator 203 acquires the AE source density distribution and the elastic wave propagation velocity distribution from another housing, and evaluates the soundness of the structure by using the acquired AE source density distribution and elastic wave propagation velocity distribution. Then, the evaluator 203 outputs the evaluation result to the display 204 provided in another housing.

By the above constitution, by using an existing device for deriving the AE source density distribution and the elastic wave propagation velocity distribution, the manufacturing cost of the structure evaluation apparatus 20 can be minimized.

The signal processor 11 may be provided in the structure evaluation apparatus 20. In this case, the signal processor 11 acquires an AE source signal processed by the AE sensor 10 directly from the AE sensor 10 or via a relay device (not illustrated).

In FIG. 1, although a single signal processor 11 is connected to the plurality of AE sensors 10-1 to 10-$n$, the structure evaluation system 100 may include a plurality of signal processors 11 and have a plurality of sensor units by the signal processors 11 being connected to the AE sensors 10, respectively.

Although the constitution in which the velocity calculator 202 derives the elastic wave propagation velocity distribution has been shown in the embodiment, the present invention is not necessarily limited thereto. For example, the velocity calculator 202 may be configured to derive a velocity in a region having a density equal to or greater than a predetermined threshold in the AE source density distribution shown in FIG. 2(A) or a velocity in a region having a density less than the predetermined threshold value. In this case, the evaluator 203 evaluates the soundness of the structure using the AE source density distribution derived by the position locator 201 and the velocity derived by the velocity calculator 202.

Further, the evaluator 203 may operate as an output control unit. The output control unit controls an output unit such that it outputs the evaluation result. Here, the output unit includes the display 204, a communication unit, and a printing unit. When the output unit is a communication unit, the output control unit controls the communication unit such feat it transmits the evaluation result to another device. Further, when the output unit is a printing unit, the output control unit controls the printing unit such that it prints the evaluation result. The structure evaluation apparatus 20 may include some or all of the display 204, the communication unit, and the printing unit as the output unit and execute the above operations.

Figure 10A:
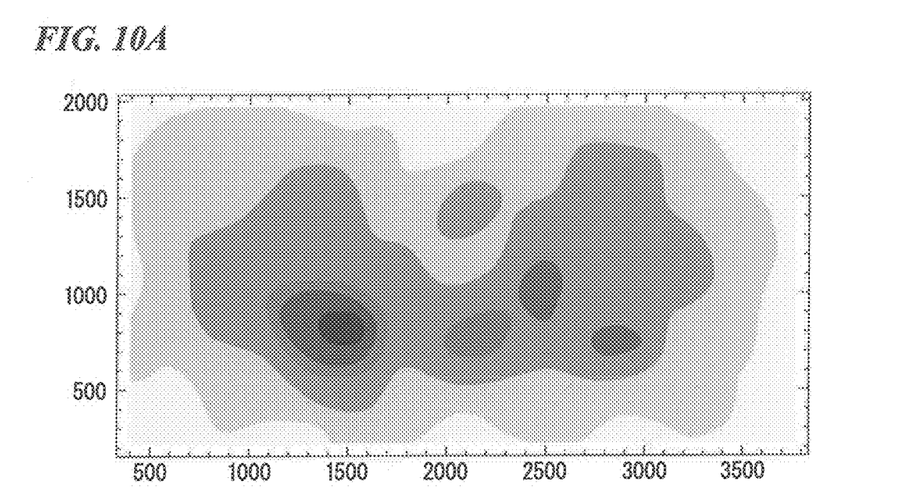
FIG. 10A is a view illustrating a result of comparing AE source density distributions.
Figure 10B:
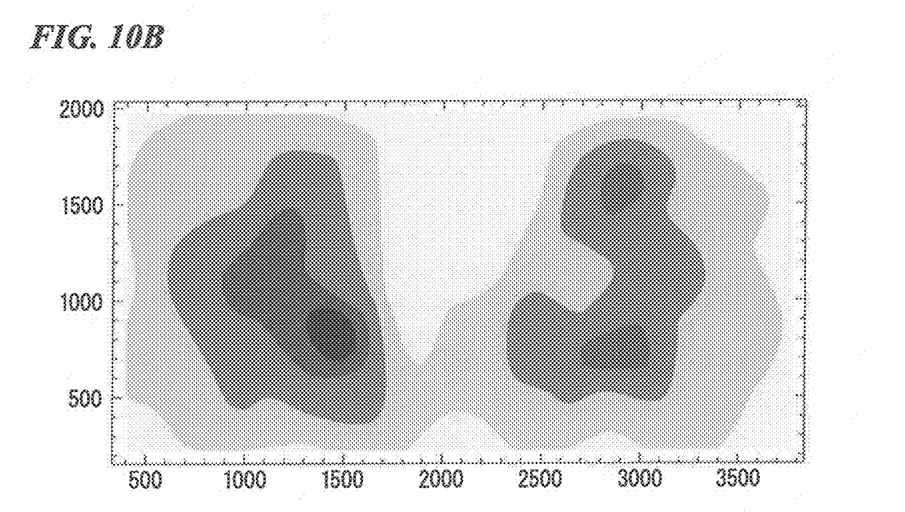
FIG. 10B is a view illustrating a result of comparing AE source density distributions.

The position locator 201 may derive the AE source density distribution using only the AE information generated from a wave source in which an amplitude of a first arrival wave of the AE is a predetermined threshold or higher. For example, the position locator 201 may derive the AE source density distribution using only AE information generated from a wave source in which an amplitude of a first arrival wave of the AE is 60 dB or more. This will be described in detail with reference to FIGS. 10A and 10B. FIG. 10A shows an AE source density distribution derived using the AE information generated from a wave source in which an amplitude of a first arrival wave of AE is 53 dB or higher, and FIG. 10B shows an AE source density distribution derived using the AE information generated from a wave source in which an amplitude of a first arrival wave of AE is 60 dB or higher. In consideration of the validity verification result of FIG. 5, more accurate evaluation can be performed by using only AE information generated from a wave source having a predetermined amplitude or higher as illustrated in FIG. 10B. Therefore, with such a constitution, it is possible to make a contribution to effective deterioration diagnosis. Also, the first arrival wave refers to an elastic wave that reaches the AE sensor first when a certain elastic wave generation event (referred to as an event) that has occurred in the structure is detected by a plurality of AE sensors.

Figure 11:
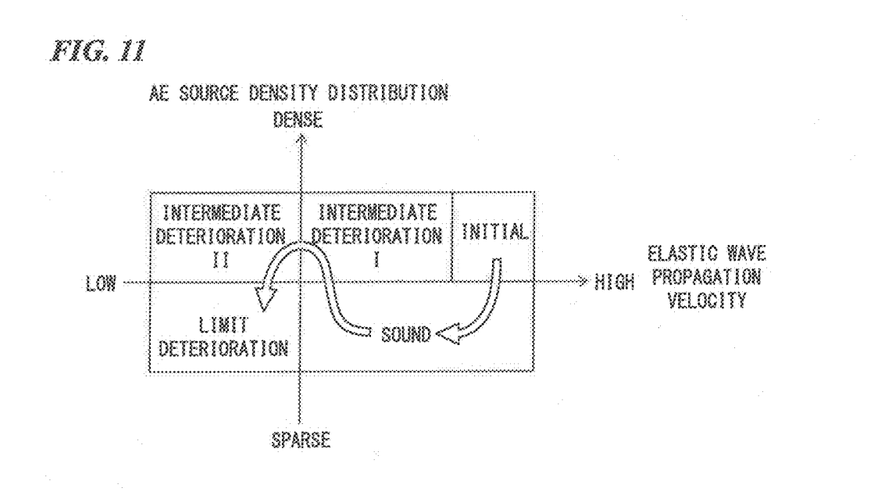
FIG. 11 is a view illustrating another example of the basic concept shown in FIG. 7.

FIG. 11 is a view illustrating another example of the basic concept shown in FIG. 7. In the example shown in FIG. 11, in addition to the distinguishing in FIG. 7. An "Initial" phase corresponding to the initial phase immediately after a structure is constructed or repaired is added. This represents a situation in which a large amount of wave sources are observed when a load is applied for the first time in the initial state after a structure is constructed or manufactured. This does not indicate that deterioration of the structure starts immediately, but indicates a response of the structure to the first load experienced by the structure. Then, the occurrence of AE decreases with respect to the past load. Therefore, the Initial phase is positioned as the preliminary phase of the Sound phase in FIG. 7, and it can be shown that, after the Initial phase, a shift toward the Sound phase occurs with a decreasing number of wave sources. For example, the example shown in FIG. 11 is a phase to be taken into consideration when soundness is evaluated immediately after a structure is constructed or repaired.

According to at least one of the embodiments described above, the soundness of a structure that generates elastic waves can be evaluated by having the plurality of AE sensors 10 configured to detect elastic waves generated from a structure, the signal processor 11 configured to perform signal processing on the elastic waves detected by the AE sensors 10 to extract an AE signal including information on the elastic waves, a position locator 201 configured to derive a wave source distribution on the basis of the AE signals, the velocity calculator 202 configured to derive a propagation velocity based on the AE signals, and the evaluator 203 configured to evaluate the soundness of the structure on the basis of the wave source distribution and the propagation velocity.

Although a few embodiments of the present invention have been described above, the embodiments are merely examples are not intended to limit the scope of the invention.

The embodiments may be implemented in various other forms, and various omissions, substitutions, and changes can be made to the embodiments within the scope not departing from the gist of the invention. The embodiments and modifications thereof belong to the claims below and their equivalents as well as the scope and gist of the invention.

REFERENCE SIGNS LIST 10 (10-1 to 10-$n$) AE sensor
11 Signal processor
20 Structure evaluation apparatus
201 Position locator
202 Velocity calculator
203 Evaluator
204 Display

The invention claimed is:

1. A structure evaluation system comprising:
a plurality of sensors configured to detect an elastic wave generated from a structure;
a position locator configured to derive a wave source distribution of elastic waves generated from the structure based on the elastic waves;
a velocity calculator configured to derive a propagation velocity of the elastic wave generated from the structure based on the elastic waves; and
an evaluator configured to:
segment a soundness of the structure into a plurality of determination regions based on a distribution reference value of the wave source distribution of the elastic wave and a velocity reference value of the propagation velocity of the elastic wave; and
evaluate the soundness of the structure based on which of the determination regions each region of the structure to be evaluated corresponds to.

2. The structure evaluation system according to claim 1, wherein, based on a reference value related to a density of the wave sources, the evaluator is further configured to:
segment the wave source distribution into two regions, including a region in which the wave sources are sparsely arranged and a region in which the wave sources are densely arranged; and
evaluate a region, in which the wave sources are sparsely arranged and the propagation velocity of the elastic wave is lower than the velocity reference value, as a region in which deterioration of the structure is most advanced.

3. The structure evaluation system according to claim 1, wherein the velocity calculator is further configured to derive a propagation velocity distribution indicating a distribution of the propagation velocity of the elastic waves by performing tomography analysis based on the elastic waves; and
the evaluator is further configured to:
segment, based on the velocity reference value, the propagation velocity distribution into two regions, including a region in which the propagation velocity is high and a region in which the propagation velocity is low; and
evaluate the region, in which the wave sources are sparsely arranged and the propagation velocity is low, as a region in which deterioration of the structure is most advanced by using the wave source distribution and the propagation velocity distribution.

4. The structure evaluation system according to claim 1, wherein the evaluator is further configured to:
evaluate each region of the structure as being in one of four phases: Sound, Intermediate deterioration I, Intermediate deterioration II, and Limit deterioration;
derive an evaluation result distribution indicating to which of the four phases among Sound, Intermediate deterioration I, Intermediate deterioration II, and Limit deterioration each of the regions of the structures corresponds; and
output the derived evaluation result distribution.

5. The structure evaluation system according to claim 2, wherein the evaluator is further configured to evaluate a region, in which the wave sources are sparsely arranged and the propagation velocity of the elastic wave is higher than the velocity reference value, as a region in the Sound phase in which deterioration of the structure is least advanced.

6. The structure evaluation system according to claim 1, wherein the position locator is further configured to derive the wave source distribution in which a distribution of the wave sources having an amplitude equal to or larger than a predetermined value is shown, based on amplitude information of the elastic waves detected by the sensors.

7. The structure evaluation system according to claim 6, wherein the amplitude Information of the elastic wave is information on an amplitude of a first arrival wave of the elastic wave in each event detected by the sensors.

8. The structure evaluation system according to claim 1, wherein the elastic wave is generated from damage to a surface or an inside of the structure as a result of stress applied to the structure.

9. A structure evaluation apparatus comprising:
a plurality of sensors configured to detect an elastic wave generated from a structure;
a position locator configured to derive a wave source distribution of elastic waves generated from the structure based on the elastic waves;
a velocity calculator configured to derive a propagation velocity of the elastic wave generated from the structure based on the elastic waves; and
an evaluator configured to:
segment a soundness of the structure into a plurality of determination regions based on a distribution reference value of the wave source distribution of the elastic wave and a velocity reference value of the propagation velocity of the elastic wave; and
evaluate the soundness of the structure based on which of the determination regions each region of the structure to be evaluated corresponds to.

10. A structure evaluation method comprising:
detecting an elastic wave generated from a structure;
deriving a wave source distribution of elastic waves generated from the structure based on the elastic waves;
deriving a propagation velocity of the elastic wave generated from the structure based on the elastic waves;
segmenting a soundness of the structure into a plurality of determination regions based on a distribution reference value of the wave source distribution of the elastic wave and a velocity reference value of the propagation velocity of the elastic wave; and
evaluating the soundness of the structure based on which of the determination regions each region of the structure to be evaluated corresponds to.

* * * * *